United States Patent [19]

Saviranta

[11] Patent Number: 6,037,185
[45] Date of Patent: Mar. 14, 2000

[54] NON-COMPETITIVE IMMUNOASSAY WITH BLOCKING OF UNOCCUPIED SPECIFIC BINDING SITES ON SOLID PHASE

[75] Inventor: Petri Saviranta, Raisio, Finland

[73] Assignees: Wallac Oy; Orion-yhtyma Oy, both of Finland

[21] Appl. No.: 09/101,358

[22] PCT Filed: Feb. 4, 1997

[86] PCT No.: PCT/FI97/00059

§ 371 Date: Jul. 8, 1998

§ 102(e) Date: Jul. 8, 1998

[87] PCT Pub. No.: WO97/29373

PCT Pub. Date: Aug. 14, 1997

[30] Foreign Application Priority Data

Feb. 6, 1996 [FI] Finland .................................. 960534

[51] Int. Cl.[7] ..................... G01N 33/566; G01N 33/557; C12Q 1/68; A61K 39/395
[52] U.S. Cl. ........................ 436/500; 436/501; 436/503; 436/504; 436/517; 436/518; 436/523; 436/524; 436/528; 436/533; 436/537; 436/541; 436/542; 436/543; 436/544; 436/545; 436/546; 435/4; 435/6; 435/7.1; 435/7.9; 435/7.92; 435/7.94; 435/7.95; 435/7.6; 435/7.8
[58] Field of Search ............................ 435/4, 6, 7.1, 7.9, 435/7.92, 7.94, 7.95, 7.6, 7.8; 436/500, 501, 503, 504, 517, 518, 523, 524, 528, 533, 537, 541, 542, 543, 544–546, 804, 815, 817, 823; 424/175.1

[56] References Cited

U.S. PATENT DOCUMENTS

| | | | |
|---|---|---|---|
| 5,476,770 | 12/1995 | Pradelles | 435/7.94 |
| 5,516,635 | 5/1996 | Ekins et al. | 435/6 |
| 5,573,920 | 11/1996 | Randle | 435/7.9 |
| 5,573,921 | 11/1996 | Behnke et al. | 435/7.92 |
| 5,710,009 | 1/1998 | Fitzpatrick et al. | 435/7.9 |
| 5,817,525 | 5/1995 | DeAlwis | 436/523 |
| 5,863,740 | 9/1995 | Kientsch-Engel et al. | 435/7.5 |

FOREIGN PATENT DOCUMENTS

WO 89/05453  6/1989  WIPO.

OTHER PUBLICATIONS

Pradelles et al., "Immunometric Assay of Low Molecular Weight Haptens Containing Primary Amino Groups," 66 *Anal. Chem.* 16–22 (1994).

Patent Abstracts of Japan, vol. 4, No. 142, p. 30 JP 55–90858, (1980) (Abstract).

*Primary Examiner*—Christopher L. Chin
*Assistant Examiner*—Pensee T. Do
*Attorney, Agent, or Firm*—Lydon & Brown, LLP

[57] ABSTRACT

A non-competitive method for the determination of analytes. Initially the analyte is bound to a specific binding partner, after which the unoccupied binding sites of the binding partner are inactivated. The bound analyte is then dissociated from the binding partner and replaced by a labeled marker, after which the bound labeled marker is determined. The signal from the bound labeled marker is directly proportional to the initial amount of analyte in the sample, which makes the present method more favorable than the competitive assays.

9 Claims, 1 Drawing Sheet

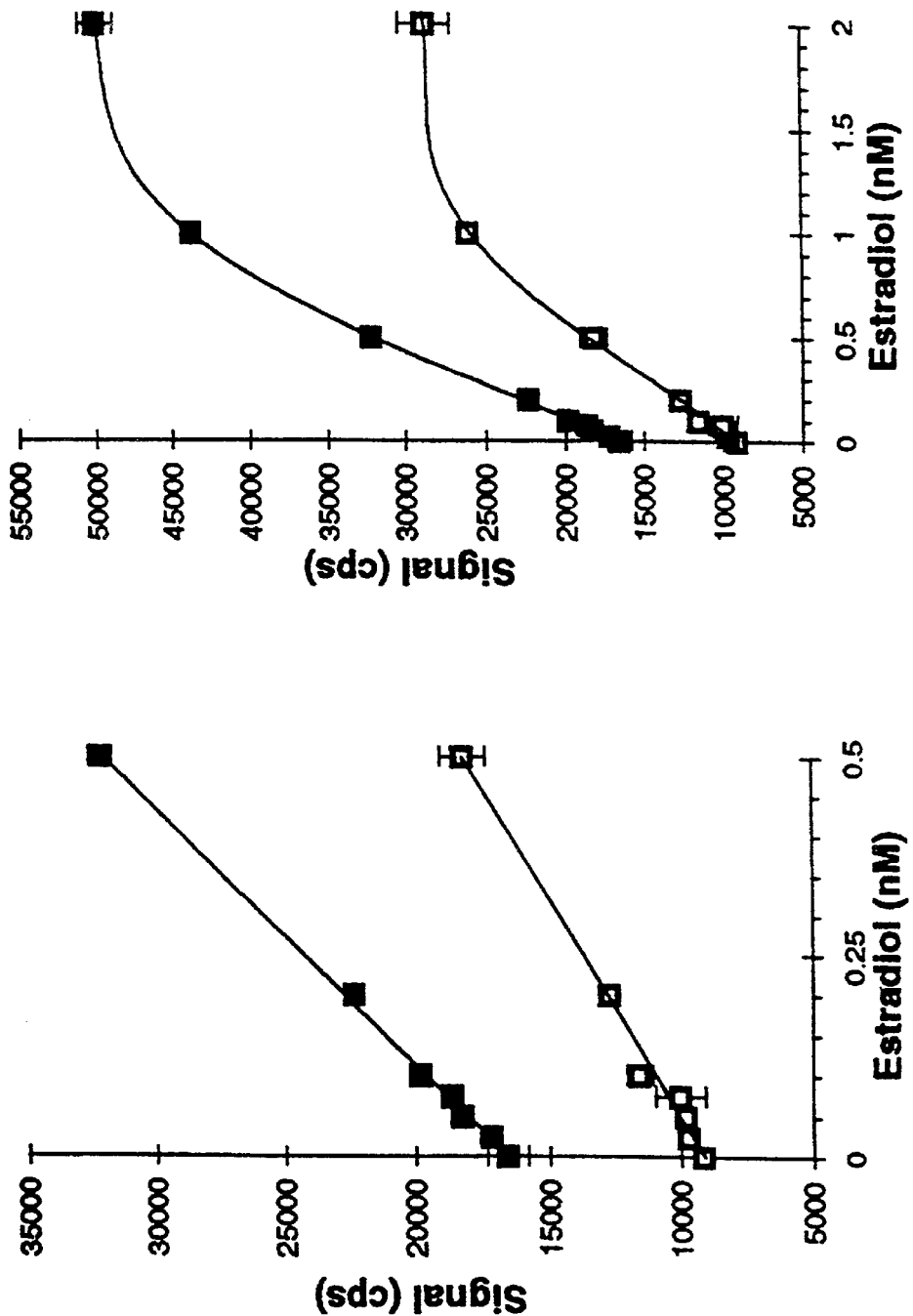

NON-COMPETITIVE IMMUNOASSAY WITH BLOCKING OF UNOCCUPIED SPECIFIC BINDING SITES ON SOLID PHASE

This application is a U.S. national stage application of International Application PCT/FI97/00059, filed Feb. 4, 1997, and claims benefit of the Feb. 6, 1996, filing date of Finnish patent application No. 960,534.

This invention relates to a method for the non-competitive determination of analytes.

BACKGROUND OF THE INVENTION

The publications and other materials used herein to illuminate the background of the invention, and in particular, cases to provide additional details with respect to the practice, are incorporated by reference.

The application of biospecific binding partners for the determination of analytes from complex samples has gained widespread use in in vitro diagnostics. At present, most of such determinations use antibodies—either polyclonal or monoclonal—as the biospecific binding partner. The determinations that use antibodies are often called immunoassays. Immunoassays are often divided into non-competitive and competitive ones, where non-competitive assays involve the use of an excess of reagents and two biospecific binding partners binding to the same analyte (this type of assay is commonly called the sandwich assay). Competitive assays on the other hand rely on the measurement of the ratio between the free and bound labelled marker, with the ratio being modified by the amount of the analyte in the sample.

In usual non-competitive immunoassays, a sample containing the antigen to be determined is incubated with an excess of a capture antibody immobilized to a solid support. A labelled antibody, specific for another epitope on the same antigen, is added in excess. A sandwich comprising "catching antibody—antigen—labelled antibody" is thus formed. After completion of the incubation, the unbound labelled antibody is removed and the signal from the label in the sandwich is measured. The signal is thus directly proportional to the antigen concentration in the sample.

The above non-competitive method cannot, however, be easily applied to the determination of small molecular weight analytes. The small molecular weight analyte is too small to simultaneously bind to two different antibodies. The immunoassay of these analytes is therefore normally performed by a competitive assay. In a typical implementation of competitive assay, the sample containing the analyte to be determined as well as a labelled derivative of the analyte are added to an immobilized antibody specific for said analyte. The unlabelled and labelled analytes compete for the binding sites on the antibody. After completion of the incubation, unbound analytes are removed and the signal from the bound labelled analyte is detected. Increased concentrations of the analyte in the sample will thus result in a decreased signal. When the signal strength is plotted as a function of increasing analyte concentration, a sigmoidal, descending curve is obtained. The sensitivity of this competitive assay is not as high as that of non-competitive assays due to the fact that the signal is at its highest value at the zero dose. As Ekins et al. [1,2] have pointed out, sensitivity can be defined as the smallest dose distinguishable from the zero dose. A usual criterion for this distinction is that the signal of the dose differs by more that two standard deviations (SD) from the signal of the zero dose. In a competitive assay one has to detect a small difference between two high signals, whereas in a non-competitive assay one has to detect a small difference between two low signals. As the SD of the low signal tends to be less than that of the high signal, the non-competitive assay is able to detect smaller differences in signal than the competitive assay. Assuming that the slopes of the dose-response curves of both assays have the same absolute value in the low dose range, then non-competitive assay is more sensitive, because its ability to detect smaller differences in signal is in direct proportion to its ability to detect smaller differences in the dose, too.

We have recently discovered a new non-competitive method for the determination of small molecular weight analytes such as haptens. Contrary to the usually employed competitive assay described above, the new method gives a linear, ascending curve when signal strength is plotted as a function of increasing analyte concentration. This key feature of the new method makes it more sensitive than the competitive immunoassay.

SUMMARY OF THE INVENTION

This invention relates to a non-competitive method for the determination of analytes, comprising the steps of a) contacting a sample containing the analyte with a binding partner specific for said analyte, b) adding a blocker, said blocker being able to inactivate the binding sites of said binding partner that are unoccupied, but not being able to inactivate the binding sites of said binding partner that are occupied by the analyte, c) dissociating the bound analyte from the binding partner, d) adding a labelled marker which is able to occupy the binding sites from which the analyte was dissociated, but which is not able to occupy the binding sites that were inactivated by the blocker, wherein step d can be performed subsequently to or simultaneously with step c, and e) measuring the signal from the labelled marker bound to the binding partner.

BRIEF DESCRIPTION OF THE DRAWINGS

FIG. 1A shows the signal strength versus concentration of 17β-Estradiol in the range 0 to 0.5 nM measured according to the method of this invention.

FIG. 1B shows the signal strength versus concentration of 17β-Estradiol in the range 0 to 2 nM measured according to the method of this invention.

In both figures the filled squares represent replacement time of 10 minutes and the open squares represent replacement time of 5 minutes.

DETAILED DESCRIPTION OF THE INVENTION

In the context of this invention the term "analyte" shall mean any molecule for which there exists a specific binding partner. The present invention is especially suited for the determination small (i.e. molecular weight less than 5000 Daltons) analytes. Such analytes are common among the groups like steroids, vitamins, prostaglandins, antiasthmatic drugs, antiarrythmic drugs, antineoplastic drugs, anticonvulsant drugs, antibiotics, antiarthritic drugs, antidepressant drugs, and drugs of abuse such as cocaine, morphine, heroin, amphetamine, methamphetamine, cannabinoids and the like, and environmental pollutants and toxins.

The "binding partner" is defined as an entity which has sufficient affinity and specificity for the analyte. Typical binding partners are macromolecules such as proteins and nucleic acids.

Proteins which are particularly suitable as binding partners include antibodies and receptors. Antibodies may be raised in animals [3] or they may be selected from recombinant libraries [4]. Antibodies specific for important analytes are commercially available from various sources. Receptors are naturally present in humans and other organisms, and they may be isolated from these sources. Alternatively, the genes coding for the receptors may be cloned by recombinant DNA technology [5], transferred to appropriate host organisms and expressed there to produce the receptor of interest [5,6]. Other naturally occurring proteins which may be suitable as binding partners are various carrier and transporting proteins, e.g. sex hormone binding globulin (SHBG). If no suitable binding partner is found among naturally existing proteins, one may be created by protein engineering, either de novo or using an existing protein as a starting material. Such protein engineering would involve either genetic engineering or chemical modifications to the protein or both.

The term "blocker" shall mean any substance that prevents the unoccupied binding partner from binding the labelled marker, but which does not prevent the occupied binding partner from liberating the analyte bound thereto and subsequently binding the labelled marker.

Preferably the blocker is a molecule exhibiting the same or similar epitope as the analyte to be determined, resulting in a mutually exclusive binding of the analyte and the blocker to the binding partner. The blocker is thus preferably, but not necessarily, a derivative of the analyte.

The blocker may also be an antibody that binds to the binding partner only when the analyte is not bound to the binding partner and which antibody, when bound to the binding partner, prevents the labelled marker from binding to the binding partner.

The blocker may also be a nucleic acid (DNA or RNA) that binds to the binding partner only when the analyte is not bound to the binding partner and which nucleic acid, when bound to the binding partner, prevents the labelled marker from binding to the binding partner.

Further, the blocker may also be a substance that modifies the unoccupied binding partner in such a fashion that it is no more able to bind the labelled marker, but which substance does not modify the occupied binding partner in such a fashion that it would not be able to liberate the analyte bound thereto and subsequently bind the labelled marker. The modifying substance may be a chemical compound or an enzyme.

A blocker that is a chemical compound may modify the binding partner by reacting with a specific residue in the binding partner. Such reactions are for example alkylation of a free cysteine residue by a maleimide derivative or a iodoacetate derivative, nitration of a tyrosine residue by tetranitromethane, bromination of a tryptophan residue by N-bromosuccinimide or the iodination of a tryptophan residue by iodine. These examples of chemical modification of the binding partner are well known to the skilled art worker, and are widely reviewed in the literature of the art. A general but not exhaustive description of these techniques is presented in reference [7]. Further, the chemical compound may be a reactive derivative of the analyte such as an aryl derivative [7], which binds to the binding partner first by biospecific recognition, and later forms a covalent bond by virtue of the reactive group. If the reactive group is an arylazide, the formation of the covalent bond can be controlled by photoactivation with ultraviolet or visible light [8].

A blocker that is an enzyme may modify the binding partner for example by digestion, by adding a phosphate, by removing a phosphate, by glycosylation or by deglycosylation. Enzymes that digest the binding partner are for example proteases, such as trypsin, pepsin, papain, factor Xa, V8 or enterokinase. Further, the enzymes that digest the binding partner may also be nucleases, if the binding partner or a part thereof is a nucleic acid (DNA or RNA). Such nucleases include for example type II restriction endonucleases, exonuclease III, DNAse I, and RNAses. Enzymes that add a phosphate are for example kinases such as a tyrosin kinase or a serine kinase. Enzymes that remove a phosphate are for example phosphatases such as LAR protein tyrosine phosphatase. Enzymes that add or remove a glycosyl group are for example glycosylases or glycosidases.

If the blocker is a molecule that binds non-covalently to the binding partner, its rate of dissociation from the binding partner must be lower than that of the analyte (at least five times as low, preferably more than one hundred times as low, most preferably more that one thousand times as low).

If the blocker is a chemical compound or an enzyme, it must be able to modify most of the unoccupied binding partners (at least more than 90%, preferably more than 95%, typically more than 99%, most preferably more than 99.8%).

The term "inactivate" shall mean any of the above listed mechanisms whereby the blocker prevents the unoccupied binding partner from binding the labelled marker.

The "marker" is a molecule which is able to bind to the binding partner only when the binding partner is not occupied by the analyte and when it is not inactivated by the blocker. Preferably, but not necessarily, the marker and the analyte bind mutually exclusively to the same binding site on the binding partner. The marker is either labelled before the replacement reaction, or it can be labelled after the replacement reaction. The label can be for example a radio-isotope, an enzyme or a fluorescent, phosphorescent or luminescent molecule.

Preferred Embodiments

The main steps of a preferred embodiment of the method according to the invention are illustrated on Scheme 1.

The method according to this invention is particularly suitable for the measurement of 17β-estradiol. In one such embodiment the analyte is 17β-estradiol, the binding partner is for example a monoclonal antibody specific for 17β-estradiol, the blocker is for example 17β-estradiol-6-carboxymethyl oxime, and the labelled marker is for example Eu-labelled 17β-estradiol-6-carboxymethyl oxime.

Although a solid phase-bound antibody is used in the examples below, the invention is not limited to this kind of embodiment. Equally well other embodiments could be devised in which the incubation of the analyte with the binding partner could take place in solution.

The invention is illuminated by the following examples.

EXAMPLE 1

Preparation of Europium-labelled 17β-Estradiol-6-carboxymethyl Oxime.

Europium chelate of 4-[2-(4-aminophenyl)ethynyl]-2,6-bis{[N,N-bis(carboxymethyl)-amino]methyl}pyridine was a gift from H. Mikola, Wallac Oy. It was synthetized by the method of Takalo et al. [9,10]. 6-oxoestradiol 6[O-(6-aminohexyl)oxime] (abbreviated 6-AHO) was a gift from H. Mikola, Wallac Oy. It was prepared according to the method of Mikola and Hänninen [11]. Europium-labelled estradiol was a gift from H. Mikola, Wallac Oy. It was synthetized from 6-AHO and the Europium chelate of 4-[2-(4-aminophenyl)ethynyl]-2,6-bis{[N,N-bis(carboxymethyl)-amino]methyl}pyridine using water soluble carbodiimide as condensation agent in a buffer-dioxane solution and purified on a gel filtration column using methods of Mikola and Miettinen [12] and Mikola et al. [13].

EXAMPLE 2

Determination of Affinity Constants (Ka) of various Monoclonal Antibodies for Europium-labelled 17β-Estradiol-6-carboxymethyl Oxime.

Three commercially available monoclonal anti-17β-estradiol antibodies were tested. These antibodies were all raised against position 6 derivatives of 17β-Estradiol. The monoclonal antibodies used were 069-A5406A (BiosPacific, California), 10-E15 (Fitzergald Industries International Inc., Massachusetts) and 2F9 (InterPharm Laboratories Ltd., Israel) and they had been raised against the following immunogens:

| Antibody | Immunogen (According to manufacturer) |
| --- | --- |
| 069-A5406A | Estradiol-6-Bovine serum albumin |
| 10-E15 | Estradiol-6-Carboxymethyloxime-carrier |
| 2F9 | Estradiol-6-Carboxymethyloxime-Bovine serum albumin |

The affinity constants of the monoclonal antibodies 069-A5406A, 10-E15 and 2F9 for Europium-labelled 17β-Estradiol-6-carboxymethyl oxime (see Example 1) were determined as follows:

All incubations were performed at 22° C. Antibodies were diluted in Assay buffer [50 mM Tris-HCl pH 7.75, 0.9% NaCl, 0.05% NaN$_3$, 0.01% Tween 40, 0.05% Bovine gammaglobulin, 20 µM Diethylenetriaminepentaacetic acid, 0.5% Bovine serum albumin, 20 µg/ml Cherry Red] at a concentration of 10 ng/ml. The diluted antibodies were placed in the wells of rabbit anti-Mouse IgG-coated microtitration strips (Wallac Oy, Turku, Finland), 200 µl per well, and the strips were shaken in a plate shaker at 600 rounds per minute for 2 hours. During the incubations, serial dilutions of Europium-labelled estradiol were made. After the incubations, the strips were washed four times with washing solution [0.9% (w/v) NaCl, 5 mM Tris-HCl pH 7.75, 0.005% Tween]. 200 µl of each dilution of the Europium-labelled estradiol were added to separate wells and the strips were shaken in a plate shaker at 600 rounds per minute for 2 hours. The strips were washed four times with washing solution, after which 200 µl of Delfia Enhancement solution (Wallac) was added. After an incubation of 30 min the time-resolved fluorescence signals were read with a Plate fluorometer (Wallac). The data were plotted as bound/free vs. bound Europium-labelled estradiol and the affinity constants were calculated from the slopes of the plots according to the method of Scatchard [14].

Results:

Affinity constants (Ka (L/mol)) for complexes between Eu-labelled 17β-Estradiol-6-carboxymethyl oxime and the various monoclonal antibodies.

| Mab | Ka |
| --- | --- |
| 069-A5406A | $6.7 \times 10^{10}$ |
| 10-E15 | $2.5 \times 10^{10}$ |
| 2F9 | $9.4 \times 10^{10}$ |

EXAMPLE 3

Determination of Half-lives of Complexes Between Various Monoclonal Antibodies and 17β-Estradiol, 17β-Estradiol-6-carboxymethyl Oxime or 17β-Estradiol-6-aminohexyl Oxime The half-lives of complexes between monoclonal antibodies (069-A5406A, 10-E15 or 2F9) and 17β-Estradiol (Sigma Chemical Company), 17β-Estradiol-6-carboxymethyl oxime (abbreviated 6-CMO; Sigma Chemical Company) or 17β-Estradiol-6-aminohexyl oxime (abbreviated 6-AHO, see Example 1) were determined as follows:

All incubations were performed at 22° C.; all dilutions were done in Assay buffer [50 mM Tris-HCl pH 7.75, 0.9% NaCl, 0.05% NaN$_3$, 0.01% Tween 40, 0.05% Bovine gammaglobulin, 20 µM Diethylenetriaminepentaacetic acid, 0.5% Bovine serum albumin, 20 µg/ml Cherry Red]. Diluted antibodies (10 ng/ml) were placed in the wells of rabbit anti-Mouse IgG-coated microtitration strips (Wallac), 200 µl per well, and the strips were shaken in a plate shaker at 600 rounds per minute for 2 hours. The strips were washed four times with washing solution [0.9% (w/v) NaCl, 5 mM Tris-HCl pH 7.75, 0.005% Tween], after which 200 µl of either 100 nM 17β-estradiol, 10 nM 6-CMO or 10 nM 6-AHO were added to the wells and the strips were shaken in a plate shaker at 600 rounds per minute for 60 min. The strips were washed four times with washing solution, after which 200 µl of 10 nM Europium-labelled 17µ-Estradiol was added. The strips were again shaken in the plate shaker at 600 rounds per minute for varying times. The strips were taken from the plate shaker one at a time and washed four times with the washing solution, after which Delfia Enhancement solution (200 µl per well; Wallac) was added. After the addition of the enhancement solution, each strip was incubated for 30 min before the time-resolved fluorescence signals were read with a Plate fluorometer (Wallac). The data were plotted as the natural logarithm of the signal (cps) vs. the elapsed time in minutes (from the addition of Europium-labelled estradiol to the start of the washes). Half-lifes were calculated from the slopes of the plots with the following formula:

Half-life (min)=[ln(2)]/−k , where k is the slope of the plot.

Results:

Half-lives (in minutes) of Mab-antigen complexes with the antiges 17β-Estradiol, 6-CMO and 6-AHO.

| Mab | Antigen | | |
| --- | --- | --- | --- |
| | 17β-Estradiol | 6-CMO | 6-AHO |
| 069-A5406A | 15 | 47 | 64 |
| 10-E15 | 9 | 127 | 93 |
| 2F9 | 44 | 51 | 154 |

For the purpose of this invention the Mab 10-E15 seemed most promising because there is a 14-fold difference between the half-lives of its complexes with 17β-Estradiol (9 min) and 6-CMO (127 min).

EXAMPLE 4

Production of a Dose-response Curve for 17β-Estradiol

All incubations were performed at 22° C.; all dilutions were done in Assay buffer [50 mM Tris-HCl pH 7.75, 0.9% NaCl, 0.05% NaN$_3$, 0.01% Tween 40, 0.05% Bovine gammaglobulin, 20 μM Diethylenetriaminepentaacetic acid, 0.5% Bovine serum albumin, 20 μg/ml Cherry Red]. Mab 10-E15 (Fitzgerald Industries International Inc., Massachusetts) was immobilized in the wells of rabbit anti-Mouse IgG-coated microtitration strips (Wallac Oy, Turku, Finland), by adding 100 μl per well of a 100 ng/ml dilution of the antibody, shaking in a plate shaker at 600 rounds per minute for 1 hour, and washing the strips four times with washing solution [0.9% (w/v) NaCl, 5 mM Tris-HCl pH 7.75, 0.005% Tween]. 100 μl per well of 17β-Estradiol standards of the concentrations 0, 0.025, 0.050, 0.075, 0.1, 0.2, 0.5 and 2 nM were added to the strips containing the immobilized antibody, after which the strips were shaken in the plate shaker at 600 rounds per minute for 2 hours. The blocking reactions were initiated by adding 100 μl per well of a 10 μM solution of 17β-estradiol-6-carboxymethyl oxime (Sigma Chemical Company). The strips were further shaken for 5 min and then washed with washing solution four times. The replacement reaction was initiated by adding 100 μl per well of 10 nM Europium-labelled 17β-estradiol, after which the strips were shaken for either 5 or 10 minutes and washed with washing solution four times. 200 μl of Delfia Enhancement solution (Wallac) was added and the plates were shaken for 30 min after which the time-resolved fluorescence signal was read with the Plate Fluorometer (Wallac).

Dose-response curves were prepared by plotting the signals against the concentrations of the standards in an X-Y plot, see FIGS. 1A and 1B. The filled squares represent replacement time of 10 minutes and the open squares represent replacement time of 5 minutes. FIG. 1A shows the curves in the concentration range 0 to 0.5 nM and FIG. 1B shows the curves over the whole measuring range of 17β-Estradiol standard concentrations. Every point shown is an average of three parallel determinations. Error bars extend±1 SD of the mean value in each point.

The least detectable dose LDD was defined as the 17β-Estradiol concentration which gives a signal that differs by two standard deviations from the zero-concentration signal. This value is calculated by dividing the standard deviation (SD) of the zero concentration signal by the slope of the linear portion of the standard curve.

It will be appreciated that the methods of the presented invention can be incorporated in the form of a variety of embodiments, only a few of which are disclosed herein. It will be apparent to the specialist that other embodiments exist and do not depart from the spirit of the invention. Thus, the described embodiments are only illustrative and should not be construed as restrictive.

SCHEME 1

1. Add sample
 - A = antigen in sample
 - coated antibody in excess =>
   A binds quantitatively

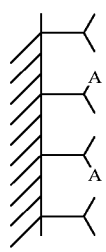

2. Add blocker
 - B = blocker = tight binding analog to antigen A
 - excess B fills all empty sites
 - wash unbound B away

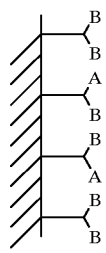

3. Add labelled marker
 - A* = labelled marker (antigen)
 - excess A* will replace A
 - tight-binding B will not be replaced
 - wash unbound A* away

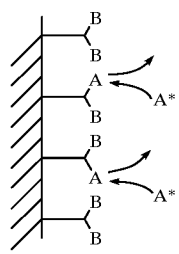

4. Measure signal
 - signal is directly proportional to original A in sample
 - will give an ascending standard curve
 - is more sensitive than competitive assay

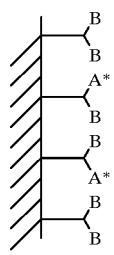

What is claimed is:

1. A method for the determination of analytes comprising the steps of
   a) contacting a sample containing said analyte with a binding partner specific for said analyte,
   b) adding a blocker, said blocker being able to inactivate the binding sites of the binding partner that are unoccupied, but not being able to inactivate the binding sites of the binding partner that are occupied by the analyte,
   c) dissociating bound analyte from the binding partner,
   d) adding a labelled marker which is able to occupy the binding sites from which the analyte was dissociated, but which is not able to occupy the binding sites that were inactivated by the blocker, wherein step d can be performed subsequently to or simultaneously with step c, and
   e) measuring a signal from the labelled marker bound to the binding partner, wherein said signal is directly proportional to an amount of said analyte originally contained in said sample.

2. The method according to claim 1 wherein the binding partner is an antibody.

3. The method according to claim 1 whe rein the binding partner is immobilized to a solid phase.

4. The method according to claim 1 wherein the blocker is bound to the binding partner by specific molecular recognition.

5. The method according to claim 4 wherein the blocker is non-covalently bound to the binding partner, and the rate of dissociation of the blocker from the binding partner is at least five times lower than the rate of dissociation of the analyte from the binding partner.

6. The method according to claim 4 wherein the blocker is covalently bound to the binding partner by virtue of a reactive group present in the blocker.

7. The method according to claim 1 wherein the blocker is a substance that chemically or enzymatically modifies the binding partner so as to inactivate its binding site.

8. The method according to claim 1 wherein the analyte is a steroid.

9. The method according to claim 8 wherein the analyte is 17β-estradiol, the blocker is 17β-estradiol-6-carboxymethyl oxime, and the labelled marker is labelled 17β-estradiol-6-carboxymethyl oxime.

* * * * *